United States Patent [19]
Prasad et al.

[11] Patent Number: 6,160,125
[45] Date of Patent: Dec. 12, 2000

[54] PROCESS FOR THE MANUFACTURE OF SULFONYLAMINOCARBONYL TRIAZOLINONES IN THE PRESENCE OF XYLENE AS SOLVENT

[75] Inventors: Vidyanatha A. Prasad, Leawood, Kans.; Klaus Jelich, Wuppertal, Germany

[73] Assignee: Bayer Corporation, Pittsburgh, Pa.

[21] Appl. No.: 09/472,685

[22] Filed: Dec. 27, 1999

[51] Int. Cl.[7] .................................................. C07D 249/12
[52] U.S. Cl. ........................................................ 548/263.4
[58] Field of Search ........................................ 548/263.4

[56] References Cited

U.S. PATENT DOCUMENTS

| | | | |
|---|---|---|---|
| 5,241,074 | 8/1993 | Daum et al. | 341/263.8 |
| 5,276,162 | 1/1994 | Muller et al. | 341/263.4 |
| 5,405,970 | 4/1995 | Daum et al. | 341/263.6 |
| 5,532,378 | 7/1996 | Daum et al. | 341/263.8 |
| 5,534,486 | 7/1996 | Müller et al. | 504/273 |
| 5,625,074 | 4/1997 | Daum et al. | 341/263.8 |
| 5,631,380 | 5/1997 | Haas et al. | 341/263.4 |
| 5,652,372 | 7/1997 | Muller et al. | 341/263.4 |
| 5,750,718 | 5/1998 | Müller et al. | 341/263.6 |
| 5,869,681 | 2/1999 | Müller et al. | 548/263.6 |

*Primary Examiner*—Patricia L. Morris
*Attorney, Agent, or Firm*—Joseph C. Gil

[57] ABSTRACT

The present invention relates to a process for manufacturing sulfonylaminocarbonyl triazolinones, which are herbicidally active compounds. In particular, this invention relates to the reaction of a substituted triazolinone with a sulfonyl isocyanate, wherein the improvement comprises conducting this reaction in the presence of xylene as solvent.

5 Claims, No Drawings

PROCESS FOR THE MANUFACTURE OF SULFONYLAMINOCARBONYL TRIAZOLINONES IN THE PRESENCE OF XYLENE AS SOLVENT

TECHNICAL FIELD OF THE INVENTION

The present invention relates to a process for manufacturing sulfonylaminocarbonyl triazolinones, which are herbicidally active compounds. In particular, this invention relates to the reaction of a substituted triazolinone with a sulfonyl isocyanate, wherein the improvement comprises conducting this reaction in the presence of xylene as solvent.

In a preferred embodiment of the invention, 2-[[[(4,5-dihydro-4-methyl-5-oxo-3-propoxy-1H-1,2,4-traizol-1-yl)carbonyl]amino]sulfonyl]-benzoic acid methyl ester (PSU) is prepared by reacting 5-propoxy-4-methyl-2,4-dihydro-3H-1,2,4-triazol-3-one (PMT) with a 2-(methoxycarbonyl) benzene sulfonyl isocyanate, in the presence of xylene as solvent.

BACKGROUND OF THE INVENTION

Sulfonylaminocarbonyl triazolinones are well known in the art, as are processes for their preparation and use as herbicides. European Patent EP-A 341,489 discloses certain substituted sulfonylaminocarbonyl triazolinones having herbicidal properties. Further, U.S. Pat. Nos. 5,534,486 and 5,869,681 describe a process for producing sulfonylaminocarbonyl triazolinones which are bonded by oxygen. The process includes the reaction of a triazolinone with a sulfonamide derivative. U.S. Pat. No. 5,750,718 describes intermediates for herbicidal sulfonylaminocarbonyl triazolinones having substituents which are bonded by sulfur.

However, the known prior art processes produce sulfonylamino-carbonyl triazolinones in unsatisfactory yield and purity. Thus, there is a need in the art for a process to manufacture sulfonylaminocarbonyl triazolinones in high yield and purity.

BRIEF SUMMARY OF THE INVENTION

The present invention is related to a process for the preparation of a sulfonylaminocarbonyl triazolinone. The process includes the reaction of a substituted triazolinone of the following general formula (I)

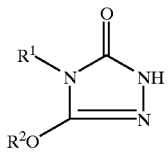

(I)

wherein
  $R^1$ and $R^2$ each represents an unsubstituted or substituted alkyl, alkenyl, alkynyl, cycloalkyl, cycloalkylalkyl, aryl or arylalkyl radical,
with a sulfonyl isocyanate of the following general formula (II)

O=C=N—SO$_2$—R$^3$       (II)

wherein
  $R^3$ represents an unsubstituted or substituted alkyl, aryl, arylalkyl or heteroaryl radical,
in the presence of xylene as solvent, to produce a sulfonylaminocarbonyl triazolinone product of the general formula (III)

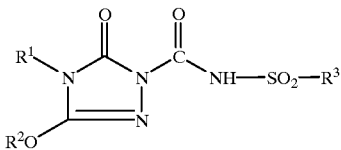

(III)

wherein $R^1$, $R^2$, and $R^3$ are as defined above.

DETAILED DESCRIPTION OF THE INVENTION

The present invention is related to a process for the preparation of a sulfonylaminocarbonyl triazolinone. The process includes the reaction of a substituted triazolinone of the following general formula (I)

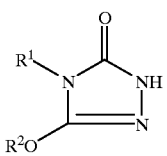

(I)

wherein
  $R^1$ and $R^2$ each represents an unsubstituted or substituted alkyl, alkenyl, alkynyl, cycloalkyl, cycloalkylalkyl, aryl or arylalkyl radical,
with a sulfonyl isocyanate of the following general formula (II)

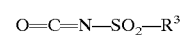

O=C=N—SO$_2$—R$^3$       (II)

wherein
  $R^3$ represents an unsubstituted or substituted alkyl, aryl, arylalkyl or heteroaryl radical,
in the presence of xylene as solvent, to produce a sulfonylaminocarbonyl triazolinone product of the general formula (III)

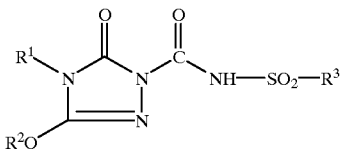

(III)

wherein $R^1$, $R^2$, and $R^3$ are as defined above.

In a preferred embodiment of the invention,
  $R^1$ represents alkyl, alkenyl or alkynyl having in each case up to 6 carbon atoms, and each of which is unsubstituted or substituted by cyano, halogen, or $C_1$–$C_4$-alkoxy,
or
  represents cycloalkyl group having 3 to 6 carbon atoms or cycloalkylalkyl group having 3 to 6 carbon atoms in the cycloalkyl moiety and 1 to 4 carbon atoms in the alkyl moiety, each of which is unsubstituted or substituted by halogen or $C_1$–$C_4$-alkyl,
or
  represents aryl group having 6 or 10 carbon atoms or arylalkyl group having 6 or 10 carbon atoms in the aryl moiety and 1 to 4 carbon atoms in the alkyl moiety, each of which is unsubstituted or substituted by carboxyl, nitro, cyano, halogen, $C_1$–$C_4$-alkyl, $C_1$–$C_4$-halogenoalkyl, $C_1$–$C_4$-alkoxy, $C_1$–$C_4$-halogenoalkoxy or $C_1$–$C_4$-alkoxy-carbonyl.

More preferably, $R^1$ represents methyl, ethyl, n- or i-propyl, n-, i-, s- or t-butyl, each of which is unsubstituted or substituted by cyano, fluorine, chlorine or bromine, methoxy or ethoxy, or represents propenyl, butenyl, propinyl or butinyl, each of which is unsubstituted or substituted by cyano, fluorine, chlorine or bromine, or represents cyclopropyl, cyclobutyl or cyclopropylmethyl, each of which is unsubstituted or substituted by fluorine, chlorine, bromine, methyl or ethyl, or represents phenyl or benzyl, each of which is unsubstituted or substituted by cyano, fluorine, chlorine, bromine, methyl, ethyl, trifluoromethyl, methoxy, ethoxy, difluoromethoxy, trifluoromethoxy, methoxycarbonyl or ethoxycarbonyl.

Most preferably, $R^1$ represents methyl.

In a preferred embodiment of the invention, $R^2$ represents alkyl, alkenyl or alkynyl, each of which has up to 6 carbon atoms, and each of which is unsubstituted or substituted by cyano, halogen or $C_1$–$C_4$-alkoxy, or represents cycloalkyl having 3 to 6 carbon atoms or cycloalkylalkyl having 3 to 6 carbon atoms in the cycloalkyl moiety and 1 to 4 carbon atoms in the alkyl moiety, each of which is unsubstituted or substituted by halogen or $C_1$–$C_4$-alkyl, or represents aryl having 6 to 10 carbon atoms or arylalkyl having 6 or 10 carbon atoms in the aryl moiety and 1 to 4 carbon atoms in the alkyl moiety, each of which is unsubstituted or substituted by carboxyl, cyano, nitro, halogen, $C_1$–$C_4$-alkyl, $C_1$–$C_4$-halogenoalkyl, $C_1$–$C_4$-alkoxy, $C_1$–$C_4$-halogenoalkoxy or $C_1$–$C_4$-alkoxy-carbonyl.

More preferably, $R^2$ represents methyl, ethyl, n- or i-propyl or n-, i-, s- or t-butyl, each of which is unsubstituted or substituted by cyano, fluorine, chlorine or bromine, methoxy or ethoxy, or represents propenyl, butenyl, propinyl or butinyl, each of which is unsubstituted or substituted by cyano, fluorine, chlorine or bromine, or represents cyclopropyl, or cyclopropylmethyl, each of which is unsubstituted or substituted by fluorine, chlorine, bromine, methyl or ethyl, or represents phenyl or benzyl, each of which is unsubstituted or substituted by cyano, fluorine, chlorine, bromine, methyl, ethyl, trifluoromethyl, methoxy, ethoxy, difluoromethoxy, trifluoromethoxy, methoxycarbonyl or ethoxycarbonyl.

Most preferably, $R^2$ represents methyl, n- or i-propyl.

In a preferred embodiment of the invention, $R^3$ represents the group

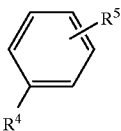

wherein $R^4$ and $R^5$ are identical or different and represent hydrogen, fluorine, chlorine, bromine, iodine, nitro, $C_1$–$C_6$-alkyl, which is unsubstituted or substituted by fluorine, chlorine, bromine, cyano, carboxyl, $C_1$–$C_4$-alkoxycarbonyl, $C_1$–$C_4$-alkylaminocarbonyl, di-($C_1$–$C_4$-alkyl)aminocarbonyl, hydroxyl, $C_1$–$C_4$-alkoxy, formyloxy, $C_1$–$C_4$-alkylcarbonyloxy, $C_1$–$C_4$-alkoxycarbonyloxy, $C_1$–$C_4$-alkylaminocarbonyloxy, $C_1$–$C_4$-alkylthio, $C_1$–$C_4$-alkylsulfinyl, $C_1$–$C_4$-alkylsulfonyl, di-($C_1$–$C_4$-alkyl)-aminosulfonyl, $C_3$–$C_6$-cycloalkyl or phenyl, or represent $C_2$–$C_6$-alkenyl which is unsubstituted or substituted by fluorine, chlorine, bromine, cyano, $C_1$–$C_4$-alkoxycarbonyl, carboxyl or phenyl, or represent $C_2$–$C_6$-alkynyl which is unsubstituted or substituted by fluorine, chlorine, bromine, cyano, $C_1$–$C_4$-alkoxycarbonyl, carboxyl or phenyl, or represent $C_1$–$C_4$-alkoxy which is unsubstituted or substituted by fluorine, chlorine, bromine, cyano, carboxyl, $C_1$–$C_4$-alkoxycarbonyl, $C_1$–$C_4$-alkoxy, $C_1$–$C_4$-alkylthio, $C_1$–$C_4$-alkylsulfinyl or $C_1$–$C_4$-alkylsulfonyl, or represent $C_1$–$C_4$-alkylthio which is unsubstituted or substituted by fluorine, chlorine, bromine, cyano, carboxyl, $C_1$–$C_4$-alkoxycarbonyl, $C_1$–$C_4$-alkylthio, $C_1$–$C_4$-alkylsulfinyl or $C_1$–$C_4$-alkylsulfonyl, or represent $C_3$–$C_6$ alkenyloxy which is unsubstituted or substituted by fluorine, chlorine, bromine, cyano or $C_1$–$C_4$-alkoxycarbonyl, or represent $C_2$–$C_6$-alkenylthio which is unsubstituted or substituted by fluorine, chlorine, bromine, cyano, nitro, $C_1$–$C_3$-aklylthio or $C_1$–$C_4$-alkoxycarbonyl, $C_3$–$C_6$-alkinyloxy, $C_3$–$C_6$-alkinylthio or the radical —S(O)$_p$—$R^6$ where p represents the numbers 1 or 2 and $R^6$ represents $C_1$–$C_4$-alkyl which is unsubstituted or substituted by fluorine, chlorine, bromine, cyano or $C_1$–$C_4$-alkoxy-carbonyl, $C_3$–$C_6$-alkenyl, $C_3$–$C_6$-alkynyl, $C_1$–$C_4$-alkoxy, $C_1$–$C_4$-alkoxy-$C_1$–$C_4$-alkylamino, $C_1$–$C_4$-alkylamino, di-($C_1$–$C_4$-alkyl)-amino, phenyl or the radical —NHOR$^7$ wherein $R^7$ represents $C_1$–$C_{12}$-alkyl which is unsubstituted or substituted by fluorine, chlorine, cyano, $C_1$–$C_4$-alkoxy, $C_1$–$C_4$-alkylthio, $C_1$–$C_4$-alkylsulfinyl, $C_1$–$C_4$-alkylsulfonyl, $C_1$–$C_4$-alkyl-carbonyl, $C_1$–$C_4$-alkoxy-carbonyl, $C_1$–$C_4$-alkylamino-carbonyl or di-($C_1$–$C_4$-alkyl)-amino-carbonyl, or represents $C_3$–$C_6$-alkenyl which is unsubstituted or substituted by fluorine, chlorine or bromine, $C_3$–$C_6$-alkynyl, $C_3$–$C_6$-cycloalkyl, C₃–C₆-cycloalkyl-C₁–C₂-alkyl, phenyl-C₁–C₂-alkyl which is unsubstituted or substituted by fluorine, chlorine, nitro, cyano, C₁–C₄-alkyl, C₁–C₄-alkoxy or C₁–C₄-alkoxy-carbonyl, or represents benzhydryl, or represents phenyl which is unsubstituted or substituted by fluorine, chlorine, nitro, cyano, C₁–C₄-alkyl, trifluoromethyl, C₁–C₄-alkoxy, C₁–C₂-fluoroalkoxy, C₁–C₄-alkylthio, trifluoromethylthio or C₁–C₄-alkoxy-carbonyl, R⁴ and/or R⁵ furthermore represent phenyl or phenoxy, or represent C₁–C₄-alkylcarbonylamino, C₁–C₄-alkoxycarbonyl-amino, C₁–C₄-alkylamino-carbonyl-amino, di-(C₁–C₄-alkyl)-amino-carbonylamino, or the radical —CO—R⁸ wherein

R⁸ represents C₁–C₆-alkyl, C₁–C₆-alkoxy, C₃–C₆-cycloalkoxy, C₃–C₆-alkenyloxy, C₁–C₄-alkylthio, C₁–C₄-alkylamino, C₁–C₄-alkoxyamino, C₁–C₄-alkoxy-C₁–C₄-alkyl-amino or di-(C₁–C₄-alkyl)-amino which are unsubstituted or substituted by halogen selected from the group consisting of fluorine and chlorine, R⁴ and/or R⁵ furthermore represent trimethylsilyl, thiazolinyl, C₁–C₄-alkylsulfonyloxy, di-(C₁–C₄-alkyl)-aminosulfonylamino or the radical —CH=N—R⁹ wherein

R⁹ represents C₁–C₆-alkyl which is unsubstituted or substituted by fluorine, chlorine, cyano, carboxyl, C₁–C₄-alkoxy, C₁–C₄-alkylthio, C₁–C₄-alkylsulfinyl or C₁–C₄-alkylsulfonyl, or represents benzyl which is unsubstituted or substituted by fluorine or chlorine, or represents C₃–C₆-alkenyl or C₃–C₆-alkynyl, each of which is unsubstituted or substituted by fluorine or chlorine, or represents phenyl which is unsubstituted or substituted by fluorine, chlorine, bromine, C₁–C₄-alkyl, C₁–C₄-alkoxy, trifluoromethyl, trifluoromethoxy or trifluoromethylthio, or represents unsubstituted or halogen-substituted C₁–C₆-alkoxy, C₃–C₆-alkenoxy, C₃–C₆-alkynoxy or benzyloxy, wherein the halogen is selected from the group consisting of fluorine and chlorine, or represents amino, C₁–C₄-alkylamino, di-(C₁–C₄-alkyl)-amino, phenylamino, C₁–C₄-alkyl-carbonylamino, C₁–C₄-alkoxy-carbonylamino or C₁–C₄-alkyl-sulfonylamino, or represents phenylsulfonylamino which is unsubstituted or substituted by fluorine, chlorine, bromine or methyl, furthermore R³ represents the radical

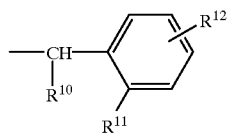

wherein

R¹⁰ represents hydrogen or C₁–C₄-alkyl,

R¹¹ and R¹² are identical or different and represent hydrogen, fluorine, chlorine, bromine, nitro, cyano, C₁–C₄-alkyl which is unsubstituted or substituted by halogen selected from the group consisting of fluorine and chlorine, C₁–C₄-alkoxy which is unsubstituted or substituted by halogen selected from the group consisting of fluorine and chlorine, carboxyl, C₁–C₄-alkoxy-carbonyl, dimethylaminocarbonyl, C₁–C₄-alkylsulfonyl or di-(C₁–C₄-alkyl)-aminosulfonyl;

furthermore

R³ represents the radical

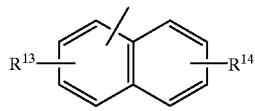

wherein

R¹³ and R¹⁴ are identical or different and represent hydrogen, fluorine, chlorine, bromine, nitro, cyano, C₁–C₄-alkyl which is unsubstituted or substituted by halogen selected from the group consisting of fluorine and chlorine or C₁–C₄-alkoxy which is unsubstituted or substituted by halogen selected from the group consisting of fluorine and chlorine;

furthermore

R³ represents the radical

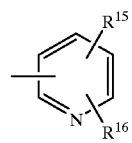

wherein

R¹⁵ and R¹⁶ are identical or different and represent hydrogen, fluorine, chlorine, bromine, nitro, cyano, C₁–C₄-alkyl which is unsubstituted or substituted by halogen selected from the group consisting of fluorine and chlorine, C₁–C₄-alkoxy which is unsubstituted or substituted by halogen selected from the group consisting of fluorine and chlorine, or represent C₁–C₄-alkylthio, C₁–C₄-alkylsulfinyl or C₁–C₄-alkylsulfonyl which are unsubstituted or substituted by halogen selected from the group consisting of fluorine and chlorine, or represent aminosulfonyl, mono-(C₁–C₄-alkyl)-aminosulfonyl, di-(C₁–C₄-alkyl)-aminosulfonyl or C₁–C₄-alkoxycarbonyl or dimethylaminocarbonyl;

furthermore

R³ represents the radical

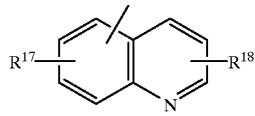

wherein

R¹⁷ and R¹⁸ are identical or different and represent hydrogen, fluorine, chlorine, bromine, C₁–C₄-alkyl which is unsubstituted or substituted by halogen selected from the group consisting of fluorine and bromine, C₁–C₄-alkoxy which is unsubstituted or substituted by halogen selected from the group consisting of fluorine and chlorine, C₁–C₄-alkylthio, C₁–C₄-alkylsulfinyl or C₁–C₄-alkylsulfonyl which are unsubstituted or substituted by halogen selected from the group consisting of fluorine and chlorine, or represent di-(C₁–C₄-alkyl)-aminosulfonyl;

furthermore

R³ represents the radical

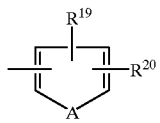

wherein
R¹⁹ and R²⁰ are identical or different and represent hydrogen, fluorine, chlorine, bromine, cyano, nitro, $C_1$–$C_4$-alkyl which is unsubstituted or substituted by halogen selected from the group consisting of fluorine and chlorine, $C_1$–$C_4$-alkoxy which is unsubstituted or substituted by halogen selected from the group consisting of fluorine and chlorine, $C_1$–$C_4$-alkylthio, $C_1$–$C_4$-alkylsulfinyl or $C_1$–$C_4$-alkysulfonyl which is unsubstituted or substituted by halogen selected from the group consisting of fluorine and chlorine, di-($C_1$–$C_4$-alkyl)-aminosulfonyl, $C_1$–$C_4$-alkoxy-carbonyl or dimethylaminocarbonyl, and A represents oxygen, sulfur or the group N—$Z^1$,
wherein
$Z^1$ represents hydrogen, $C_1$–$C_4$-alkyl which is unsubstituted or substituted by fluorine, chlorine, bromine, or cyano, $C_3$–$C_6$-cycloalkyl, benzyl, phenyl which is unsubstituted or substituted by fluorine, chlorine, bromine or nitro, $C_1$–$C_4$-alkylcarbonyl, $C_1$–$C_4$-alkoxycarbonyl or di-($C_1$–$C_4$-alkyl)-amino-carbonyl;
furthermore
R³ represents the radical

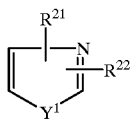

wherein
R²¹ and R²² are identical or different and represent hydrogen, $C_1$–$C_4$-alkyl, halogen, $C_1$–$C_4$-alkoxycarbonyl, $C_1$–$C_4$-alkoxy or $C_1$–$C_4$-halogenoalkoxy,
$Y^1$ represents sulfur or the group N—R²³
wherein
R²³ represents hydrogen or $C_1$–$C_4$-alkyl;
furthermore
R³ represents the radical

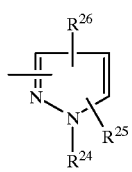

wherein
R²⁴ represents hydrogen, $C_1$–$C_4$-alkyl, benzyl, pyridyl, quinolinyl or phenyl,
R²⁵ represents hydrogen, halogen, cyano, nitro, $C_1$–$C_4$-alkyl which is unsubstituted or substituted by halogen selected from the group consisting of fluorine and chlorine, $C_1$–$C_4$-alkoxy which is unsubstituted or substituted by halogen selected from the group consisting of fluorine and chlorine, dioxolanyl or $C_1$–$C_4$-alkoxy-carbonyl and R²⁶ represents hydrogen, halogen or $C_1$–$C_4$-alkyl;
furthermore
R³ represents a compound selected from the group consisting of

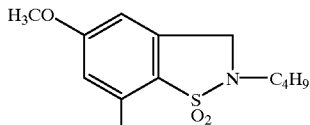

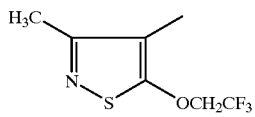

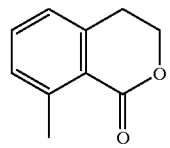

The invention furthermore preferably relates to the sodium, potassium, magnesium, calcium, ammonium, $C_1$–$C_4$-alkyl-ammonium, di-($C_1$–$C_4$-alkyl)-ammonium, tri-($C_1$–$C_4$-alkyl)-ammonium, $C_5$- or $C_6$-cycloalkyl-ammonium and di-($C_1$–$C_2$-alkyl)-benzyl-ammonium salts of the formula (IV) in which R¹, R² and R³ have the meanings mentioned above as being preferred.

In particular, the invention relates to compounds of the formula (IV)
wherein
R¹ represents hydrogen, amino, $C_1$–$C_4$-alkyl which is unsubstituted or substituted by fluorine, cyano, methoxy or ethoxy, or represents allyl, $C_3$–$C_6$-cycloalkyl, benzyl, phenyl, $C_1$–$C_3$-alkylamino, $C_3$–$C_6$-cycloalkylamino or di-($C_1$–$C_3$-alkyl)-amino,
R² represents $C_1$–$C_4$-alkyl which is unsubstituted or substituted by halogen selected from the group consisting of fluorine and chlorine, methoxy or ethoxy, or represents $C_3$–$C_4$-alkenyl which is unsubstituted or substituted by halogen selected from the group consisting of fluorine and chlorine, or represents $C_3$–$C_6$-cycloalkyl, or represents benzyl which is unsubstituted or substituted by a compound selected from the group consisting of fluorine, chlorine and methyl, and
R³ represents the group

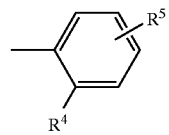

wherein
R⁴ represents fluorine, chlorine, bromine, methyl, trifluoromethyl, methoxy, difluoromethoxy, trifluoromethoxy, 2-chloro-ethoxy, 2-methoxy-ethoxy, $C_1$–$C_3$-alkythio, $C_1$–$C_3$-alkysulphinyl, $C_1$–$C_3$-alkylsulfonyl, dimethylamino-sulfonyl, diethylaminosulfonyl, N-methoxy-N-methyl-aminosulfonyl, methoxyaminosulfonyl, phenyl, phenoxy or $C_1$–$C_3$-alkoxy-carbonyl and
R⁵ represents hydrogen, fluorine, chlorine or bromine;
furthermore $R^3$ represents the radical

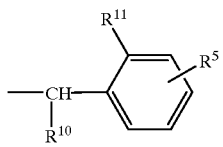

wherein
$R^{10}$ represents hydrogen,
$R^{11}$ represents fluorine, chlorine, bromine, methyl, methoxy, difluoromethoxy, trifluorormethoxy, ethoxy, methoxycarbonyl, ethoxycarbonyl, methylsulfonyl or dimethylaminosulfonyl and
$R^{12}$ represents hydrogen,
furthermore
$R^3$ represents the radical

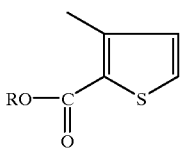

wherein
R represents $C_1$–$C_4$-alkyl, or represents the radical

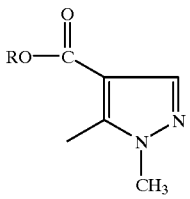

wherein
R represents $C_1$–$C_4$-alkyl.

The process according to the invention is generally carried out at atmospheric pressure. However, it is also possible to conduct the process under elevated or reduced pressure.

The reaction of the substituted triazolinone (formula I) with the sulfonyl isocyanate (formula II) to produce the sulfonylaminocarbonyl triazolinone product (formula III), is carried out at a temperature of from about −20° C. to about 120° C., and preferably at a temperature of from about 0° C. to about 45° C.

The reaction time to produce the intermediate product is up to about 48 hours, and preferably from about 1 hour to about 8 hours.

In the process of the invention, suitable sulfonyl isocyanates include 2-(trifluoromethoxy) benzensulfonyl isocyanate, 2-(methoxycarbonyl)benzenesulfonyl isocyanate, benzenesulfonyl isocyanate, p-toluenesulfonyl isocyanate, 2-fluoro, 2-chloro-, 2-bromo-, 2-methyl-, 2-methoxy-, 2-trifluoromethyl-, 2-difluoro-methoxy-, 2-trifluoro-methoxy-, 2-methylthio-, 2-ethylthio-, 2-propylthio-, 2-methylsulfinyl-, 2-methyl-sulfonyl-, 2-dimethylaminosulfonyl-, 2-diethylamino-sulfonyl-, 2-(N-methoxy-N-methyl-aminosulfonyl-, 2-phenyl-, 2-phenoxy-, 2-methoxycarbonyl-, 2-ethoxycarbonyl, 2-propoxycarbonyl- and 2-isopropoxycarbonyl-phenylsulfonyl isocyanate, 2-fluoro-, 2-chloro-, 2-difluoromethoxy-, 2-trifluoro-methoxy-, 2-methoxycarbonyl- and 2-ethoxycarbonyl-benzylsulfonyl isocyanate, 2-methoxycarbonyl-3-thienyl-sulfonyl isocyanate, 4-methoxycarbonyl- and 4-ethoxy-carbonyl-1-methyl-pyrazol-5-yl-sulfonyl isocyanate.

In a preferred embodiment, the sulfonyl isocyanate is 2-(trifluoro-methoxy)benzenesulfonyl isocyanate or 2-(methoxycarbonyl)-benzenesulfonyl isocyanate.

The molar ratio of substituted triazolinone to sulfonyl isocyanate is from about 1.0:0.5 to about 1.0:1.1, and preferably from about 1.0:0.9 to about 1.0:1.0.

The invention is further illustrated but is not intended to be limited by the following examples in which all parts and percentages are by weight unless otherwise specified.

EXAMPLES

Example 1

Synthesis and Isolation of PSU Using MIBK as Solvent

To a 500 ml flask with mechanical stirrer, thermometer, and dry nitrogen inlet, was charged 15.7 grams (0.097 mole) of 97% pure PMT and 80 grams of methyl isobutyl ketone (MIBK). To this mixture was added 45.8 grams (0.095 mole) of 50% pure 2-(methoxycarbonyl) benzene sulfonyl isocyanate in MIBK, over a time period of 1 hour and at a temperature of about 25° C. The reaction temperature was increased from about 25° C. to a temperature of from about 40° C. to about 45° C., and the mixture was cooked for about 6 hours. The mixture was then cooled to about 10° C. and the solids were isolated by filtration. The solids were washed with about 100 grams of water at 20° C. The solids were then isolated and washed with about 25 grams of MIBK at a temperature of from about 10° C. to about 15° C. The isolated solids were then filtered and air-dried until free of water and MIBK. The net yield of PSU based on the isocyanate was 83.5% (with 98.5% purity).

Example 2

Synthesis and Isolation of PSU Using Xylene as Solvent

To a 500 ml flask with mechanical stirrer, thermometer, and dry nitrogen inlet, was charged 15.7 grams (0.097 mole) of 97% pure PMT and 80 grams of xylene. To this mixture was added 45.8 grams (0.095 mole) of 50% pure 2-(methoxycarbonyl)benzene sulfonyl isocyanate in xylene, over a time period of 1 hour and at a temperature of about 25° C. The reaction temperature was increased from about 25° C. to a temperature of from about 40° C. to about 45° C. and the mixture was cooked for about 6 hours. The mixture was then cooled to a temperature of about 10° C. and the solids were isolated by filtration. The solids were washed with about 100 grams of water at a temperature of about 20° C. The solids were then isolated ad washed with about 25 grams of xylenes at a temperature of from about 10° C. to about 15° C. The isolated solids were then filtered and air-dried until free of water and xylenes. The net yield of PSU based on the isocyanate was 96.5% with 98.7% purity.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for preparing a sulfonylaminocarbonyl triazolinone comprising the step of:

reacting a substituted triazolinone of the following general formula

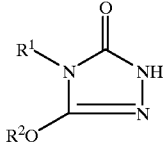

(I)

wherein
$R^1$ and $R^2$ each represents an unsubstituted or substituted alkyl, alkenyl, alkynyl, cycloalkyl, cycloalkylalkyl, aryl or arylalkyl radical,
with a sulfonyl isocyanate of the following general formula (II)

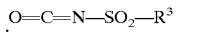

(II)

wherein
$R^3$ represents an unsubstituted or substituted alkyl, aryl, arylalkyl or heteroaryl radical,
in the presence of xylene as solvent, to produce a sulfonylaminocarbonyl triazolinone product of the general formula (III)

(III)

wherein $R^1$, $R^2$, and $R^3$ are as defined above.

2. The process of claim 1 wherein the reaction is carried out at a temperature of from about −20° C. to about 120° C.

3. The process of claim 1 wherein the reaction is carried out at a temperature of from about 0° C. to about 45° C.

4. The process of claim 1 wherein the sulfonyl isocyanate is selected from the group consisting of 2-(trifluoromethoxy) benzenesulfonyl isocyanate and 2-(methoxycarbonyl) benzenesulfonyl isocyanate.

5. The process of claim 1 wherein the substituted triazolinone to sulfonyl isocyanate is from about 1.0:0.5 to about 1.0:1.1.

* * * * *